US009439578B2

(12) United States Patent
Thakur et al.

(10) Patent No.: US 9,439,578 B2
(45) Date of Patent: Sep. 13, 2016

(54) ARTIFACT CANCELLATION TO SUPPRESS FAR-FIELD ACTIVATION DURING ELECTROPHYSIOLOGY MAPPING

(71) Applicant: Boston Scientific Scimed, Inc., Maple Grove, MN (US)

(72) Inventors: Pramodsingh H. Thakur, Woodbury, MN (US); Shantha Arcot-Krishnamurthy, Renton, WA (US); Barun Maskara, Blaine, MN (US); Sunipa Saha, Shoreview, MN (US); Allan C. Shuros, St. Paul, MN (US); Shibaji Shome, Arden Hills, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/136,378

(22) Filed: Dec. 20, 2013

(65) Prior Publication Data

US 2014/0187991 A1 Jul. 3, 2014

Related U.S. Application Data

(60) Provisional application No. 61/746,160, filed on Dec. 27, 2012.

(51) Int. Cl.
*A61B 5/0456* (2006.01)
*A61B 5/0452* (2006.01)
(Continued)

(52) U.S. Cl.
CPC ............ *A61B 5/0452* (2013.01); *A61B 5/0422* (2013.01); *A61B 5/6858* (2013.01);
(Continued)

(58) Field of Classification Search
CPC ............ A61B 5/04525; A61B 5/6858; A61B 5/7203
USPC .................................................. 600/509–510
See application file for complete search history.

(56) References Cited

U.S. PATENT DOCUMENTS 4,407,296 A   10/1983 Anderson
4,962,767 A * 10/1990 Brownlee ..................... 607/122
(Continued)

FOREIGN PATENT DOCUMENTS

CN       1253761 A    5/2000
CN     200960161 Y   10/2007
(Continued)

OTHER PUBLICATIONS

International Search Report and Written Opinion issued in PCT/US2013/076958, mailed Apr. 7, 2014, 14 pages.
(Continued)

*Primary Examiner* — George Evanisko
(74) *Attorney, Agent, or Firm* — Faegre Baker Daniels LLP (57) ABSTRACT

A method for mapping a cardiac chamber includes sensing activation signals of intrinsic physiological activity with a plurality of electrodes disposed in or near the cardiac chamber, the activation signals including a near-field activation signal component and a far-field activation signal component, isolating R-wave events in the activation signals, generating a far-field activation template representative of the far-field activation signal component based on the R-wave events, and filtering the far-field activation template from the activation signals to identify the near-field activation signal components in the activation signals.

16 Claims, 6 Drawing Sheets

(51) Int. Cl.
  *A61B 5/00*   (2006.01)
  *A61N 1/37*   (2006.01)
  *A61B 5/042*  (2006.01)
  *A61N 1/05*   (2006.01)
(52) U.S. Cl.
  CPC ............ *A61B5/7203* (2013.01); *A61N 1/056* (2013.01); *A61N 1/3702* (2013.01); *A61B 5/0456* (2013.01); *A61B 5/725* (2013.01); *A61B 5/7282* (2013.01)

(56) References Cited

U.S. PATENT DOCUMENTS

| | | | |
|---|---|---|---|
| 5,647,870 | A | 7/1997 | Kordis et al. |
| 5,683,425 | A | 11/1997 | Hauptmann |
| 5,772,693 | A * | 6/1998 | Brownlee ............... 607/123 |
| 5,776,072 | A * | 7/1998 | Hsu et al. ............... 600/518 |
| 5,782,898 | A * | 7/1998 | Dahl et al. ............... 607/119 |
| 5,817,133 | A * | 10/1998 | Houben ............... 607/9 |
| 6,070,094 | A | 5/2000 | Swanson et al. |
| 6,214,025 | B1 | 4/2001 | Thistle et al. |
| 6,233,491 | B1 | 5/2001 | Kordis et al. |
| 6,650,931 | B1 | 11/2003 | McClure et al. |
| 6,660,021 | B1 | 12/2003 | Palmer et al. |
| 6,735,465 | B2 | 5/2004 | Panescu |
| 6,810,283 | B2 * | 10/2004 | Suribhotla et al. ........... 600/509 |
| 7,338,512 | B2 | 3/2008 | McGuckin, Jr. et al. |
| 7,672,722 | B1 | 3/2010 | Mengotto |
| 7,780,694 | B2 | 8/2010 | Palmer et al. |
| 7,850,708 | B2 | 12/2010 | Pal |
| 7,933,643 | B1 | 4/2011 | Gill et al. |
| 8,019,409 | B2 | 9/2011 | Rosenberg et al. |
| 8,055,333 | B2 | 11/2011 | Duann et al. |
| 8,060,202 | B2 | 11/2011 | Betzold et al. |
| 8,090,434 | B2 * | 1/2012 | Lian et al. ............... 600/515 |
| 8,155,739 | B2 | 4/2012 | Keel et al. |
| 8,165,666 | B1 | 4/2012 | Briggs et al. |
| 8,175,693 | B2 | 5/2012 | Rosenberg et al. |
| 8,195,292 | B2 | 6/2012 | Rosenberg et al. |
| 8,543,195 | B1 | 9/2013 | Brockway et al. |
| 9,131,866 | B2 | 9/2015 | Thakur et al. |
| 2003/0236466 | A1 | 12/2003 | Tarjan et al. |
| 2004/0176694 | A1 * | 9/2004 | Kim et al. ............... 600/510 |
| 2005/0154321 | A1 | 7/2005 | Wolinsky et al. |
| 2005/0209678 | A1 | 9/2005 | Henkes et al. |
| 2005/0288600 | A1 | 12/2005 | Zhang et al. |
| 2006/0253044 | A1 | 11/2006 | Zhang et al. |
| 2008/0243214 | A1 | 10/2008 | Koblish |
| 2008/0281369 | A1 | 11/2008 | KenKnight et al. |
| 2009/0240157 | A1 | 9/2009 | Lian et al. |
| 2009/0254140 | A1 | 10/2009 | Rosenberg et al. |
| 2009/0306732 | A1 | 12/2009 | Rosenberg et al. |
| 2009/0318995 | A1 | 12/2009 | Keel et al. |
| 2010/0152801 | A1 | 6/2010 | Koh et al. |
| 2010/0256699 | A1 | 10/2010 | Makdissi |
| 2010/0268059 | A1 | 10/2010 | Ryu et al. |
| 2011/0054559 | A1 | 3/2011 | Rosenberg et al. |
| 2011/0054560 | A1 | 3/2011 | Rosenberg et al. |
| 2011/0066201 | A1 | 3/2011 | Rosenberg et al. |
| 2011/0066202 | A1 | 3/2011 | Rosenberg et al. |
| 2011/0066203 | A1 | 3/2011 | Rosenberg et al. |
| 2011/0092809 | A1 | 4/2011 | Nguyen et al. |
| 2011/0118803 | A1 | 5/2011 | Hou et al. |
| 2011/0144510 | A1 | 6/2011 | Ryu et al. |
| 2011/0184274 | A1 | 7/2011 | Rosenberg et al. |
| 2011/0213260 | A1 | 9/2011 | Keel et al. |
| 2011/0251505 | A1 | 10/2011 | Narayan et al. |
| 2011/0295137 | A1 | 12/2011 | Rosenberg et al. |
| 2011/0319954 | A1 | 12/2011 | Niazi et al. |
| 2012/0157865 | A1 | 6/2012 | Stein et al. |
| 2012/0184863 | A1 | 7/2012 | Harlev et al. |
| 2012/0327204 | A1 * | 12/2012 | Friedman et al. ............ 348/65 |
| 2013/0274582 | A1 | 10/2013 | Afonso et al. |
| 2013/0345537 | A1 | 12/2013 | Thakur et al. |
| 2013/0345577 | A1 | 12/2013 | Thakur et al. |
| 2013/0345583 | A1 | 12/2013 | Thakur et al. |
| 2014/0018792 | A1 | 1/2014 | Gang et al. |
| 2014/0067279 | A1 | 3/2014 | George et al. |
| 2014/0187991 | A1 | 7/2014 | Thakur et al. |
| 2014/0316294 | A1 | 10/2014 | Maskara et al. |
| 2015/0257671 | A1 | 9/2015 | Laughner et al. |
| 2015/0342536 | A1 | 12/2015 | Kovtun et al. |

FOREIGN PATENT DOCUMENTS

| | | |
|---|---|---|
| CN | 101365379 A | 2/2009 |
| CN | 101558993 A | 10/2009 |
| EP | 1543865 A1 | 6/2005 |
| EP | 2863792 A1 | 4/2015 |
| EP | 2863793 A1 | 4/2015 |
| WO | WO2000047278 A1 | 8/2000 |
| WO | WO2000045700 A1 | 8/2000 |
| WO | WO2011041489 | 4/2001 |
| WO | WO03022356 A2 | 3/2003 |
| WO | WO2006037172 A1 | 4/2006 |
| WO | WO2008118992 A1 | 10/2008 |
| WO | WO2011075328 A1 | 6/2011 |
| WO | 2014058484 A1 | 4/2014 |
| WO | 2015187371 A1 | 12/2015 |

OTHER PUBLICATIONS

International Preliminary Report on Patentability issued in PCT/US2013/076958, mailed Jun. 30, 2015, 8 pages.

International Search Report and Written Opinion issued in International Application No. PCTIUS2013/046843, mailed Oct. 23, 2013, 12 pages.

International Search Report and Written Opinion issued in PCT/US2013/046841, mailed Oct. 15, 2013, 12 pages.

International Search Report and Written Opinion issued in PCT/US2015/031787, mailed Aug. 5, 2015, 11 pages.

Potter, M. et al., "Competing ICA Techniques in Biomedical Signal Analysis", Electrical and Computer Enoineering, 2001, Canadian Conference on May 13-16, 2001, Piscataway, NJ, USA, IEEE, vol. 2, May 13, 2001, pp. 987-992.

Zhou, Yu et al., "A New United Analysis Method for Epicardial Mapping Signals", Bioinformatics and Biomedical Engineering, 2008, ICBBE 2008, the Second International Conference, IEEE, Piscataway, NJ, USA, May 16, 2008, pp. 636-639.

* cited by examiner

ARTIFACT CANCELLATION TO SUPPRESS FAR-FIELD ACTIVATION DURING ELECTROPHYSIOLOGY MAPPING

CROSS-REFERENCE TO RELATED APPLICATIONS

This application claims the benefit under 35 U.S.C. section 119(e) to U.S. Provisional Application 61/746,160, entitled "ARTIFACT CANCELLATION TO SUPPRESS FAR-FIELD ACTIVATION DURING ELECTROPHYSIOLOGY MAPPING", filed on Dec. 27, 2012, which is herein incorporated by reference in its entirety.

TECHNICAL FIELD

The present disclosure relates to cardiac mapping systems. More specifically, the present disclosure relates to a cardiac mapping system configured to suppress far-field activation during mapping with signal artifact cancellation.

BACKGROUND

Diagnosing and treating heart rhythm disorders often involve the introduction of a catheter having a plurality of sensors/probes into a cardiac chamber through the surrounding vasculature. The sensors detect electric activity of the heart at sensor locations in the heart. The electric activity is generally processing into electrogram signals that represent signal propagation through cardiac tissue at the sensor locations.

The sensors in cardiac chamber may detect far-field electrical activity, i.e. the ambient electrical activity away from the sensors, which can negatively affect the detection of local electrical activity, signals at or near the sensor location. For example, ventricular activation may present itself as far-field signals substantially simultaneously on multiple sensors situated in the atrium. Due to the magnitude of ventricular activations, the phenomenon can mask significant aspects of highly localized atrial activity and thus portray inaccurate activation maps and/or reduced resolution activation maps upon which physicians rely to administer therapy, e.g. ablation therapy, to a patient.

SUMMARY

In Example 1, a method for mapping a cardiac chamber includes sensing activation signals of intrinsic physiological activity with a plurality of electrodes disposed in or near the cardiac chamber, the activation signals including a near-field activation signal component and a far-field activation signal component, isolating far-field events in the activation signals, generating a far-field activation template representative of the far-field activation signal component based on the isolated far-field events, and filtering the far-field activation template from the activation signals to identify the near-field activation signal components in the activation signals.

In Example 2, the method according to Example 1, wherein the step of isolating R-wave events in the activation signals includes obtaining a reference timing for far-field events, and segmenting the activation signals sensed by each electrode around far-field events according to the obtained reference timing.

In Example 3, the method according to either Example 1 or 2, wherein the far-field event corresponds to a ventricular activation signal and the reference timing corresponds to at least one of a Q-wave and an R-wave event in an electrogram.

In Example 4, the method according to any of Examples 1-3, wherein the step of generating a far-field activation template includes averaging the far-field events in the segmented activation signals from each electrode.

In Example 5, the method according to any of Examples 1-4, wherein the step of filtering the far-field activation template from the activation signals includes subtracting the far-field activation template from the activation signals at or near the isolated far-field events.

In Example 6, the method according to any of Examples 1-5, wherein, prior to subtracting the far-field activation template, the step of filtering the far-field activation template from the activation signals further includes fitting an amplitude of the far-field template to correspond to an amplitude of each isolated far-field event.

In Example 7, the method according to any of Examples 1-6, wherein the step of filtering the far-field activation template from the activation signals includes identifying a time period during which the far-field activation signal component is present, and filtering the far-field activation template only during the time period.

In Example 8, the method according to any of Examples 1-7, further including averaging the far-field activation template with far-field activation signal components during a predetermined number of subsequent far-field events to update the far-field activation template.

In Example 9, the method according to any of Examples 1-8, wherein the filtering step includes blanking electrodes in the array based on a comparison of an amplitude of the generated far-field template and an amplitude of the sensed far-field signals.

In Example 10, a method for reconstructing electrical activity propagation along an electrode array within a cardiac chamber includes sensing activation signals of intrinsic physiological activity with a plurality of electrodes disposed in or near the cardiac chamber, the activation signals including a near-field activation signal component and a far-field activation signal component, isolating far-field events in the activation signals, generating a far-field activation template representative of the far-field activation signal component based on isolated far-field events, filtering the far-field activation template from the activation signals to identify the near-field activation signal components in the activation signals, and mapping the identified near-field activation signal components.

In Example 11, the method according to either Examples 9 or 10, wherein the step of isolating the far-field event in the activation signal includes obtaining a reference timing for far-field events, and segmenting the activation signals sensed by each electrode around far-field events according to the obtained reference timing in the activation signals.

In Example 12, the method according to any of Examples 9-11, wherein the far-field event corresponds to a ventricular activation signal and the reference timing to at least one of a Q-wave and an R-wave event in an electrogram.

In Example 13, the method according any one of Examples 9-12, wherein the step of generating a far-field activation template includes averaging the far-field events in the segmented activation signals from each electrode.

In Example 14, the method according to any one of Examples 9-13, wherein the step of filtering the far-field activation template from the activation signals includes subtracting the far-field activation template from the activation signals at or near the isolated far-field events.

In Example 15, the method according any one of Examples 9-14, prior to subtracting the far-field activation template, the step of filtering the far-field activation template from the activation signals further includes fitting an amplitude of the far-field template to correspond to an amplitude of each isolated far-field event.

In Example 16, the method according any one of Examples 9-15, wherein the step of filtering the far-field activation template from the activation signals includes identifying a time period during which the far-field activation signal component is present, and filtering the far-field activation template only during the time period.

In Example 17, the method according any one of Examples 9-16, further including averaging the far-field activation template with far-field activation signal components during a predetermined number of subsequent R-wave events to update the far-field activation template.

In Example 18, the method according to any of Examples 9-17, wherein the filtering step includes blanking electrodes in the array based on a comparison of an amplitude of the generated far-field template and an amplitude of the sensed far-field signals.

In Example 19, a catheter system according to Example 18, including a plurality of mapping electrodes configured to sense activation signals of intrinsic physiological activity disposed in or near the cardiac chamber, the activation signals including a near-field activation signal component and a far-field activation signal component, and a processing system associated with the plurality of mapping electrodes, the signal processing system configured to isolate far-field events in the activations and generate a far-field activation template representative of the far-field activation signal component based on the far-field events, the processing system further configured to filter the far-field activation template from the activation signals to identify the near-field activation signal components in the activation signals and to map the identified near-field activation signal component.

In Example 20, the catheter system according to Example 19, wherein the processing system is further configured to obtain a reference timing for far-field events, segment the activation signals sensed by each electrode around far-field events according to the obtained reference timing to isolate the R-wave event in the activation signal, average the isolated far-field events in the segmented activation signals from each electrode to generate the far-field activation template, and subtract the far-field activation template from the activation signals at or near the isolated far-field events to filter the far-field activation template from the activation signals.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
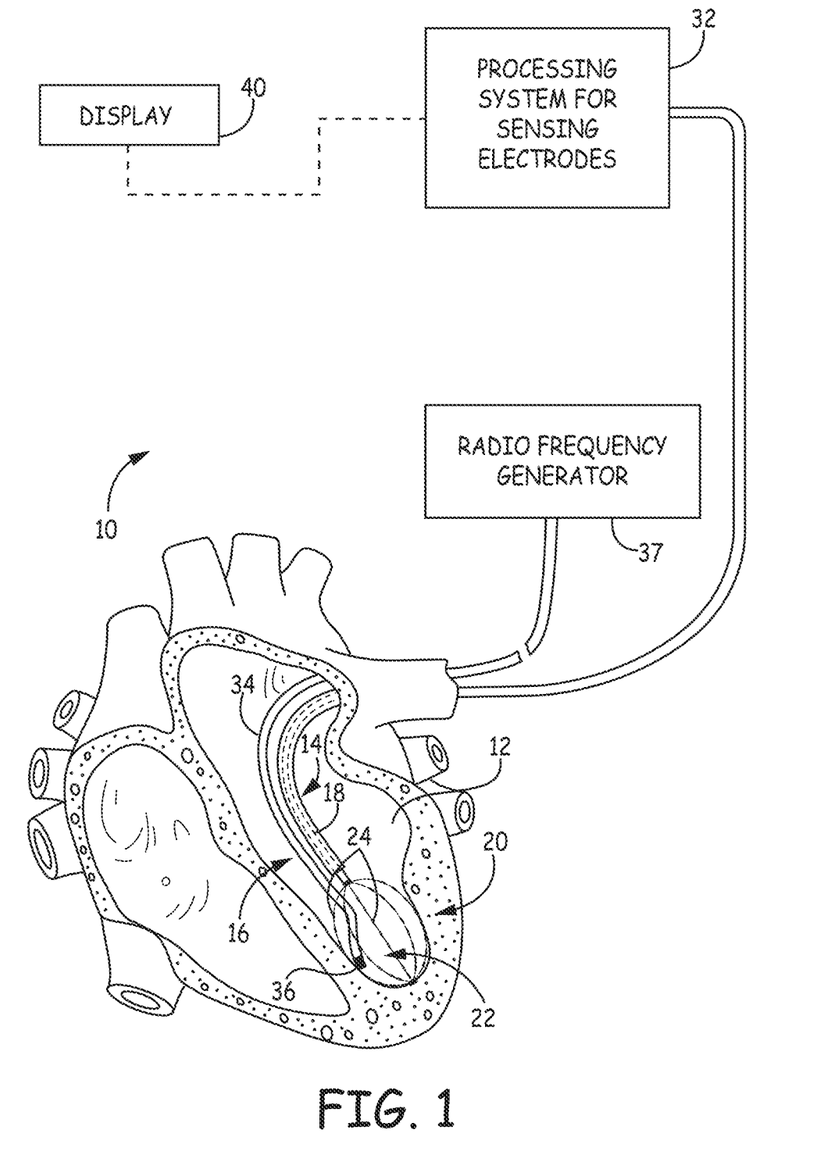
FIG. 1 a schematic view of an embodiment of a catheter system for accessing a targeted tissue region in the body for diagnostic and therapeutic purposes.

FIG. 1 is a schematic view of a system 10 for accessing a targeted tissue region in the body for diagnostic or therapeutic purposes. FIG. 1 generally shows the system 10 deployed in the left ventricle of the heart. Alternatively, system 10 can be deployed in other regions of the heart, such as the left atrium, right atrium, or right ventricle. While the illustrated embodiment shows the system 10 being used for ablating myocardial tissue, the system 10 (and the methods described herein) may alternatively be configured for use in other tissue ablation applications, such as procedures for ablating tissue in the prostrate, brain, gall bladder, uterus, and other regions of the body, including in systems that are not necessarily catheter-based.

The system 10 includes a mapping probe 14 and an ablation probe 16. In FIG. 1, each is separately introduced into the selected heart region 12 through a vein or artery (e.g., the femoral vein or artery) through suitable percutaneous access. Alternatively, the mapping probe 14 and ablation probe 16 can be assembled in an integrated structure for simultaneous introduction and deployment in the heart region 12.

The mapping probe 14 has a flexible catheter body 18. The distal end of the catheter body 18 carries a three-dimensional multiple electrode structure 20. In the illustrated embodiment, the structure 20 takes the form of a basket defining an open interior space 22 (see FIG. 2), although other multiple electrode structures could be used wherein the geometry of the electrode structure and electrode locations are known. The multiple electrode structure 20 carries a plurality of electrodes 24 wherein each is configured to sense intrinsic physiological activity in the anatomical region on which the ablation procedure is to be performed. In some embodiments, the electrodes are configured to detect activation signals of the intrinsic physiological activity within the anatomical structure, e.g., the activation times of cardiac activity.

The electrodes 24 are electrically coupled to a processing system 32. A signal wire (not shown) is electrically coupled to each electrode 24 on the basket structure 20. The wires extend through the body 18 of the probe 14 and electrically couple each electrode 24 to an input of a mapping processor 33 of the processing system 32, as will be described later in greater detail. The electrodes 24 sense intrinsic electrical activity in the anatomical region, e.g., myocardial tissue that has both a near-field activation signal component and a far-field activation component. The sensed activity is processed by the signal processing system 32 to assist the physician in identifying a near-field activation component signal. The near-field activation signal component can be further analyzed to find the presence of a pathology and to determine a location suitable for ablation for treatment of the pathology, e.g. ablation therapy.

In some embodiments, the processing system 32 may be configured to measure the intrinsic electrical activity in the myocardial tissue adjacent to the electrodes 24. For example, in some embodiments, the processing system 32 is configured to detect intrinsic electrical activity associated with a pathological dominant rotor in the anatomical feature being mapped. Studies have shown that dominant rotors have a role in the initiation and maintenance of atrial fibrillation, and ablation of the rotor path and/or rotor core may be effective in terminating the atrial fibrillation.

The ablation probe 16 includes a flexible catheter body 34 that carries one or more ablation electrodes 36. The one or more ablation electrodes 36 are electrically connected to a radio frequency generator (RF) 37 that is configured to deliver ablation energy to the one or more ablation electrodes 36. The ablation probe 16 is movable with respect to the anatomical feature to be treated, as well as the structure 20. The ablation probe 16 is positionable between or adjacent to electrodes 24 of the structure 20 as the one or more ablation electrodes 36 are positioned with respect to the tissue to be treated. Once positioned, the physician directs the RF generator 37 to supply the ablation electrode 36 with a predetermined amount of ablation energy. In response, the ablation electrode 36 emits ablating energy to cauterize the contacted tissue and disrupt the abnormal electrical pathways, i.e. dominant rotors.

In the illustrated embodiment, the processing system 32 includes an output display device 40 (e.g., a CRT, LED display, or a printer). The device 40 presents a graphical representation of the intrinsic physiological activity to the physician which may be useful for remotely guiding the ablation electrode 36 within the basket structure 20.

Figure 2:
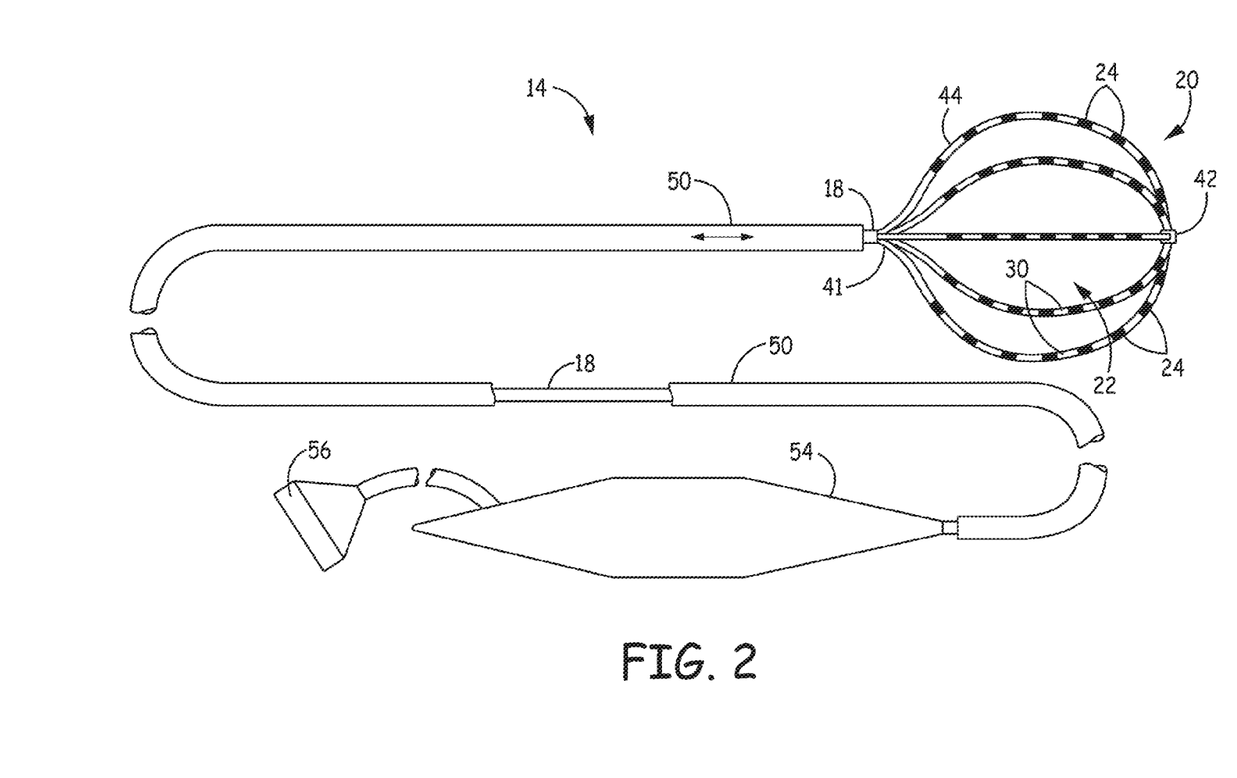
FIG. 2 is a schematic view of an embodiment of a mapping catheter having a basket functional element carrying structure for use in association with the system of FIG. 1.

FIG. 2 illustrates an embodiment of the mapping catheter 14 including electrodes 24 at the distal end suitable for use in the system 10 shown in FIG. 1. The mapping catheter 14 has a flexible catheter body 18, the distal end of which carries the three dimensional structure 20 configured to carry the mapping electrodes or sensors 24. The mapping electrodes 24 sense intrinsic electrical activity in the myocardial tissue, the sensed activity is then processed by the processing system 32 to assist the physician in identifying the site or sites having a heart rhythm disorder or other myocardial pathology. This process is commonly referred to as mapping. This information can then be used to determine an appropriate location for applying appropriate therapy, such as ablation, to the identified sites, and to navigate the one or more ablation electrodes 36 to the identified sites.

The illustrated three-dimensional structure 20 comprises a base member 41 and an end cap 42 between which flexible splines 44 generally extend in a circumferentially spaced relationship. As discussed above, the three dimensional structure 20 takes the form of a basket defining an open interior space 22. In some embodiments, the splines 44 are made of a resilient inert material, such as Nitinol metal or silicone rubber, and are connected between the base member 41 and the end cap 42 in a resilient, pretensed condition, to bend and conform to the tissue surface they contact. In the illustrated embodiment, eight splines 44 form the three dimensional structure 20. Additional or fewer splines 44 could be used in other embodiments. As illustrated, each spline 44 carries eight mapping electrodes 24. Additional or fewer mapping electrodes 24 could be disposed on each spline 44 in other embodiments of the three dimensional structure 20. In the illustrated embodiment, the three dimensional structure 20 is relatively small (e.g., 40 mm or less in diameter). In alternative embodiments, the three dimensional structure 20 is larger (e.g., 40 mm in diameter or greater).

In some embodiments, a slidable sheath 50 is movable along the major axis of the catheter body 30. Moving the sheath 50 forward (i.e., toward the distal end) causes the sheath 50 to move over the three dimensional structure 20, thereby collapsing the structure 20 into a compact, low profile condition suitable for introduction into an interior space, such as, for example, into the heart. In contrast, moving the sheath 50 rearward (i.e., toward the proximal end) exposes the three dimensional structure 20, allowing the structure 20 to elastically expand and assume the pretensed position illustrated in FIG. 2. Further details of embodiments of the three dimensional structure 20 are disclosed in U.S. Pat. No. 5,647,870, entitled "Multiple Electrode Support Structures," which is hereby incorporated by reference in its entirety.

A signal wire (not shown) is electrically coupled to each mapping electrode 26. The wires extend through the body 30 of the mapping catheter 20 into a handle 54, in which they are coupled to an external connector 56, which may be a multiple pin connector. The connector 56 electrically couples the mapping electrodes 24 to the processing system 32. Further details on mapping systems and methods for processing signal generated by the mapping catheter are discussed in U.S. Pat. No. 6,070,094, entitled "Systems and Methods for Guiding Movable Electrode Elements within Multiple-Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are incorporated herein by reference.

It is noted that other multi-electrode structures could be deployed on the distal end. It is further noted that the multiple mapping electrodes 24 may be disposed on more than one structure rather than, for example, the single mapping catheter 14 illustrated in FIG. 2. For example, if mapping within the left atrium with multiple mapping structures, an arrangement comprising a coronary sinus catheter carrying multiple mapping electrodes and a basket catheter carrying multiple mapping electrodes positioned in the left atrium may be used. As another example, if mapping within the right atrium with multiple mapping structures, an arrangement comprising a decapolar catheter carrying multiple mapping electrodes for positioning in the coronary sinus, and a loop catheter carrying multiple mapping electrodes for positioning around the tricuspid annulus may be used.

Although the mapping electrodes 24 have been described as being carried by dedicated mapping probes, such as the mapping catheter 14, the mapping electrodes may be carried on non-mapping dedicated probes or multifunction probes. For example, an ablation catheter, such as the ablation catheter 16, can be configured to include one or more mapping electrodes 24 disposed on the distal end of the catheter body and coupled to the signal processing system 32. As another example, the ablation electrode at the distal end of the ablation catheter may be coupled to the signal processing system 32 to also operate as a mapping electrode.

Figure 4:
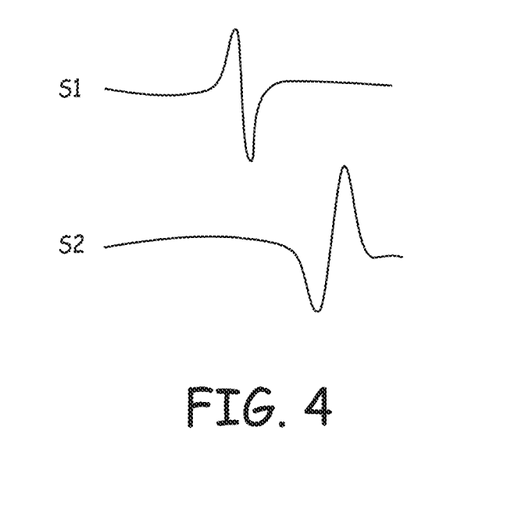
FIG. 4 illustrates an example of an R-wave event plot of two channels from mapping elements of the basket functional elements as a function of time.

To illustrate the operation of the system 10, FIG. 4 is a schematic side view of an embodiment of the basket structure 20 including a plurality of mapping electrodes 24. In the illustrated embodiment, the basket structure includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on a basket structure 20, the mapping electrodes 24 may alternatively be arranged in different numbers, on different structures, and/or in different positions. In addition, multiple basket structures can be deployed in the same or different anatomical structures to simultaneously obtain signals from different anatomical structures.

Figure 3:
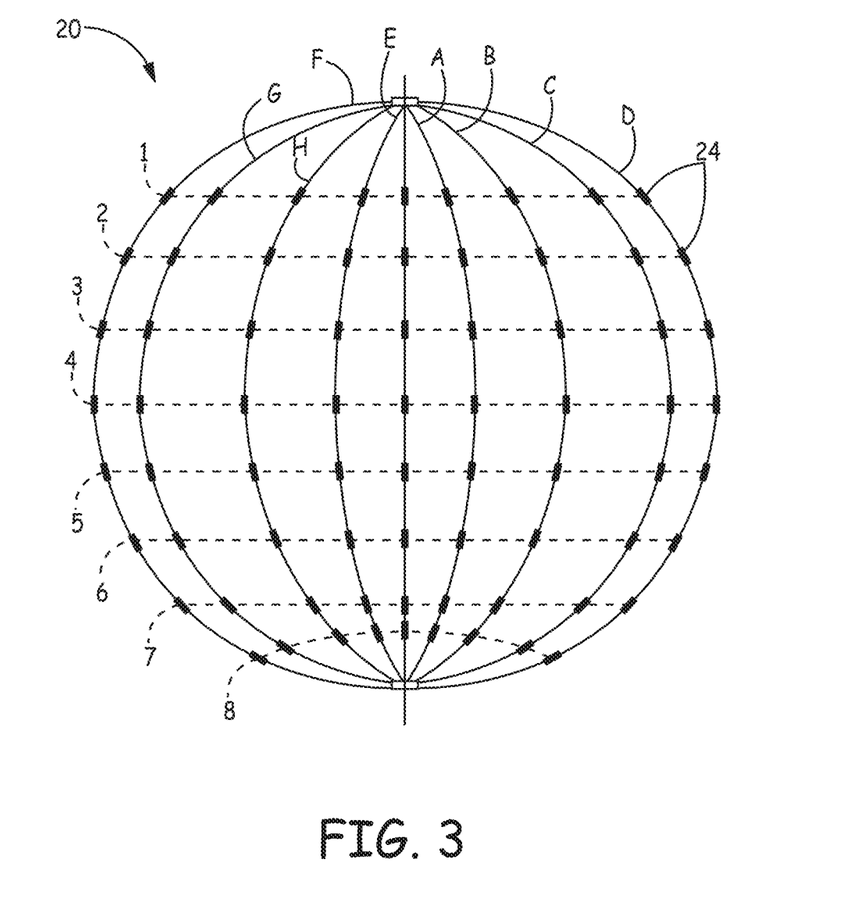
FIG. 3 is a schematic side view of an embodiment of the basket functional element including a plurality of mapping electrodes.

In various embodiments, signals sensed by mapping electrodes 24 can be plotted to generate a multi-dimensional representation of signals from multiple elements or channels. FIG. 4 illustrates an example of a plot of an R-wave event from two channels (S1, S2) of the mapping electrodes 24 as a function of time. For example, in the embodiment of the mapping catheter illustrated in FIGS. 2 and 3, channels S1 and S2 may be activation signals from a selected two of the sixty-four mapping elements 26.

After the basket structure 20 is positioned adjacent to the anatomical structure to be treated (e.g., left atrium, left ventricle, right atrium, or right ventricle of the heart), the processing system 32 receive activation signals from the electrodes 24 related to intrinsic physiological activity of the anatomical structure, i.e. the electrodes 24 measure electrical activation signals intrinsic to the physiology of the anatomical structure. The acquired activation signals can be processed by processing system 32 to suppress a far-field activation signal component, i.e. activation signals due to global activation, to enhance a near-field activation signal component, i.e. signals associated with local activation. Far-field activity can interfere with local activity by masking and/or enhancing local activity which may in turn lead to an improper diagnosis by a physician. An example of far-field activity during an atrial procedure, which are interested activation signals originating from atrial tissue, includes, but not limited to, cardiac activation signals which originate from ventricular tissue. The vice versa also holds, when performing a ventricular procedure, the activation signals originating from the atrium can interfere with local ventricular activation signals.

Figure 5:
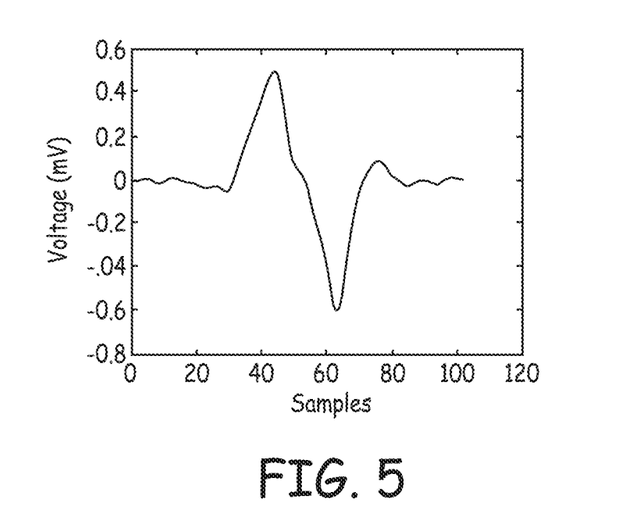
FIG. 5 illustrates an example of a far-field activation signal averaged across a plurality of samples.
Figure 6:
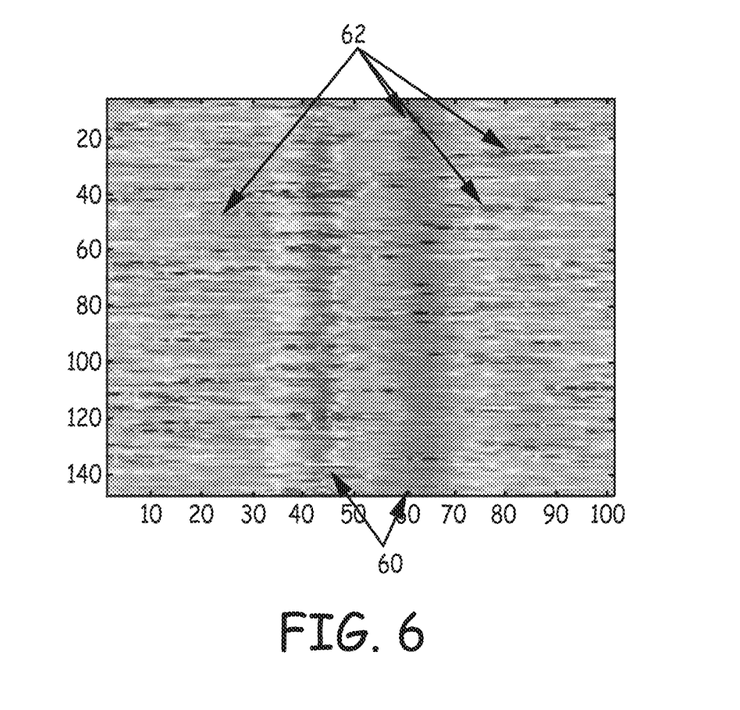
FIG. 6 illustrates an example of an amplitude plot of a plurality of R-wave events segmented from acquired activation signals.
Figure 7:
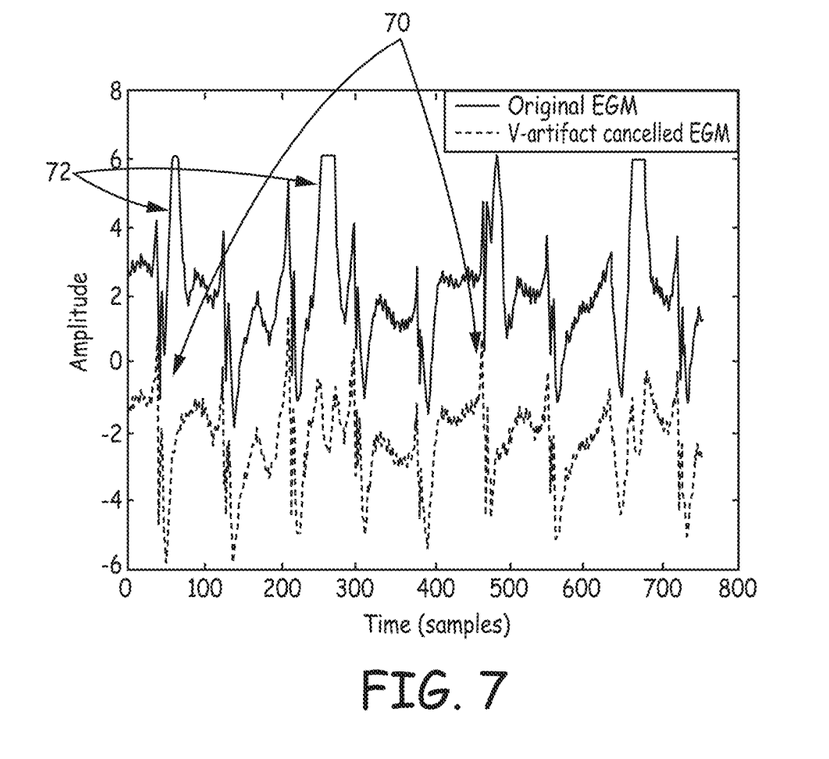
FIG. 7 illustrates an example of an original activation signal and a corresponding filtered activation signal.

To suppress or filter the far-field activation signals, the processing system 32 generates a far-field template and filters the far-field activation signal component from the acquired activation signals based on the far-field template. The far-field template is representative of the far-field activation signal component of the acquired activation signals, e.g. ventricular activity during an atrial study. The template is generated by isolating afar-field event in the acquired activation signals for each channel. The far-field event can be isolated by segmenting or windowing around each event according to an obtained reference timing. The reference timing corresponds to at least one of a Q-wave event or an R-wave event detected in an electrogram, e.g. based on an intracardiac electrogram or a surface electrode electrogram. The isolated far-field event is then averaged across the samples from each channel to generate the far-field template. For example, FIG. 5 illustrates an example far-field template generated from isolated far-field events averaged across a plurality of samples. The averaging reduces random non-deterministic far-field events which maybe the result of a pathology. For example, during atrial fibrillation local activation signals are irregular from beat to beat while the far-field ventricular activation signals remain regular. The averaging of the isolated far-field events reduces the random atrial activation signal while retaining the regular ventricular activation signal. FIG. 6 illustrates an example of an amplitude map of each activation signal (plotted on the horizontal axis) as a function of samples (plotted on the vertical axis) wherein the regular far-field ventricular activation signals 60 are shown as definite higher-intensity bands and the irregular near-field atrial activation signals 62 appear as noise. FIG. 7 illustrates an electrocardiogram before and after far-field activation suppression where local near-field activations 70 were originally masked by far-field activations 72.

The processing system 32 filters the far-field activation signals to identify the near-field activation signal components, i.e. local activation signals, by subtracting the far-field activation template from the activation signals acquired from each mapping electrode 24 channel at or near the isolated far-field events. To account for variations in local activation signal amplitudes with respect to the far-field activation template, the processing system 32 can perform an amplitude fitting function, such as a least square fit, to adjust the amplitude of the far-field template to match the amplitude of the activation signal substantially at or near each isolated far-field event on the acquired activation signal data.

In some embodiments, the processing system 32 can update the far-field template as activation signals are acquired to account for gradual drifts or changes over time prior to filtering. For example, the far-field activation template can be generated according to activation signals acquired during the most recent N cardiac activations, i.e. the last N cardiac activation signals or heartbeats are employed for the template generation.

In some embodiments, the processing system 32 can generate the far-field activation template based on activation signals acquired from a selected subset of mapping electrode 24 channels. For example, far-field ventricular activation signals are prominent in the proximal atrial sensors, i.e. closer towards the base member 41, rather than the distal atrial sensors, i.e. closer towards the end cap 42. Therefore, the processing system 32 can generate the far-field activation template based on activation signals sensed by the proximal atrial sensors rather than the distal atrial sensors.

In some embodiments, the processing system 32 can disable or blank one or more channels of the mapping electrodes 24 that are susceptible to irregular far-field activations. Channels with detected far-field activations that have consistent amplitudes among consecutive activation signals, i.e. from beat to beat, can be reliably filtered or suppressed by the processing system 32. However, channels with detected far-field activations that have inconsistent amplitudes from among consecutive activation signals are not reliably filtered by the processing system 32. Therefore, the processing system 32 may disable or blank the corresponding channel because the activation signal data may lead to erroneous diagnoses. To determine which channels should be disabled, the processing system 32 compares the amplitudes from consecutive far-field activations after the segmentation of the corresponding far-field event.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for mapping a cardiac chamber, the method comprising:
sensing activation signals of intrinsic physiological activity with a plurality of electrodes disposed in or near the cardiac chamber, the activation signals including a near-field activation signal component and a far-field activation signal component, wherein the plurality of electrodes are disposed on a catheter;
isolating far-field events in the activation signals;
segmenting the activation signals sensed by each electrode;
generating a far-field activation template representative of the far-field activation signal component by averaging the far-field events in the segmented activation signals from each electrode;
comparing amplitudes among a set of consecutive far-field segmented activation signals corresponding to an electrode of the plurality of electrodes;
determining that the consecutive far-field segmented activation signals have inconsistent amplitudes;
blanking the electrode in the plurality of electrodes based on determining that the consecutive far-field segmented activation signals have inconsistent amplitudes; and
subtracting the far-field activation template from the activation signals at the isolated far-field events to identify the near-field activation signal components in the activation signals.

2. The method according to claim 1, wherein the step of segmenting the activation signals sensed by each electrode comprises:
obtaining a reference timing for far-field events; and
segmenting the activation signals sensed by each electrode around far-field events according to the obtained reference timing.

3. The method according to claim 2, wherein the far-field event corresponds to a ventricular activation signal and the reference timing corresponds to at least one of a Q-wave and an R-wave event in an electrogram.

4. The method according to claim 1, wherein, prior to subtracting the far-field activation template, the step of filtering the far-field activation template from the activation signals further comprises:
fitting an amplitude of the far-field template to correspond to an amplitude of each isolated far-field event.

5. The method according to claim 1, wherein the step of filtering the far-field activation template from the activation signals comprises:
identifying a time period during which the far-field activation signal component is present; and
filtering the far-field activation template only during the time period.

6. The method according to claim 1, and further comprising:
averaging the far-field activation template with far-field activation signal components during a predetermined number of subsequent far-field events to update the far-field activation template.

7. The method according to claim 1, further comprising:
selecting a subset of the plurality of electrodes based on the location on the catheter of the subset of the plurality of the electrodes;
wherein the step of isolating far-field events in the activation signals comprises isolating far-field events in the activation signals sensed by the subset of the plurality of electrodes.

8. The method according to claim 1, wherein the catheter comprises a mapping catheter.

9. A method for reconstructing electrical activity propagation along an electrode array within a cardiac chamber, the method comprising:
sensing activation signals of intrinsic physiological activity with a plurality of electrodes disposed in or near the cardiac chamber, the activation signals including a near-field activation signal component and a far-field activation signal component, wherein the plurality of electrodes are disposed on a catheter;
isolating far-field events in the activation signals;
segmenting the activation signals sensed by each electrode;
generating a far-field activation template representative of the far-field activation signal component by averaging the far-field events in the segmented activation signals from each electrode;
subtracting the far-field activation template from the activation signals at the isolated far-field events to identify the near-field activation signal components in the activation signals;
comparing amplitudes among a set of consecutive far-field segmented activation signals corresponding to an electrode of the plurality of electrodes;
determining that the consecutive far-field segmented activation signals have inconsistent amplitudes;
blanking the electrode in the plurality of electrodes based on determining that the consecutive far-field segmented activation signals have inconsistent amplitudes; and
mapping the identified near-field activation signal components.

10. The method according to claim 9, wherein the step of segmenting the activation signals sensed by each electrode comprises:
obtaining a reference timing for far-field events; and
segmenting the activation signals sensed by each electrode around far-field events according to the obtained reference timing in the activation signals.

11. The method according to claim 10, wherein the far-field event corresponds to a ventricular activation signal and the reference timing to at least one of a Q-wave and an R-wave event in an electrogram.

12. The method according to claim 9, wherein, prior to subtracting the far-field activation template, the step of filtering the far-field activation template from the activation signals further comprises:
fitting an amplitude of the far-field template to correspond to an amplitude of each isolated far-field event.

13. The method according to claim 9, wherein the step of filtering the far-field activation template from the activation signals comprises:
identifying a time period during which the far-field activation signal component is present; and
filtering the far-field activation template only during the time period.

14. The method according to claim 9, and further comprising:
averaging the far-field activation template with far-field activation signal components during a predetermined number of subsequent R-wave events to update the far-field activation template.

15. A catheter system comprising:
a catheter;
a plurality of mapping electrodes disposed on the catheter and configured to sense activation signals of intrinsic physiological activity disposed in or near the cardiac chamber, the activation signals including a near-field activation signal component and a far-field activation signal component; and
a signal processing system associated with the plurality of mapping electrodes, the signal processing system configured to isolate far-field events in the activations, segment the activation signals sensed by each electrode and average the isolated far-field events in the segmented activation signals from each electrode to generate a far-field activation template representative of the far-field activation signal component, the processing system further configured to subtract the far-field activation template from the activation signals at the isolated far-field events to identify the near-field activation signal components in the activation signals, to compare amplitudes among a set of consecutive far-field segmented activation signals corresponding to an electrode of the plurality of electrodes, to determine that the consecutive far-field segmented activation signals have inconsistent amplitudes, to blank the electrode in the plurality of electrodes based on determining that the consecutive far-field segmented activation signals have inconsistent amplitudes, and to map the identified near-field activation signal component.

16. The catheter system according to claim 15, wherein when the processing device segments the activation signals sensed by each electrode, the processing system is configured to obtain a reference timing for far-field events and segment the activation signals sensed by each electrode around far-field events according to the obtained reference timing to isolate the R-wave event in the activation signal.

* * * * *